US009689861B1

(12) United States Patent
Nickerson et al.

(10) Patent No.: US 9,689,861 B1
(45) Date of Patent: Jun. 27, 2017

(54) CONCRETE TEST CYLINDER MOLD, SYSTEM, AND METHOD OF USE

(71) Applicant: Concrete Block Insulating Systems, Inc., West Brookfield, MA (US)

(72) Inventors: David L. Nickerson, Wilbraham, MA (US); Paul W. Grycel, Sarasota, FL (US)

(*) Notice: Subject to any disclaimer, the term of this patent is extended or adjusted under 35 U.S.C. 154(b) by 0 days.

(21) Appl. No.: 15/182,872

(22) Filed: Jun. 15, 2016

Related U.S. Application Data

(63) Continuation-in-part of application No. 14/732,842, filed on Jun. 8, 2015.

(51) Int. Cl.
| | | |
|---|---|---|
| *G01N 3/00* | (2006.01) | |
| *G01N 33/38* | (2006.01) | |
| *B28B 1/14* | (2006.01) | |
| *B28B 13/06* | (2006.01) | |
| *B28B 7/00* | (2006.01) | |
| *B28B 11/24* | (2006.01) | |
| *G01N 3/08* | (2006.01) | |

(52) U.S. Cl.
CPC ............ *G01N 33/383* (2013.01); *B28B 1/14* (2013.01); *B28B 7/0082* (2013.01); *B28B 7/0094* (2013.01); *B28B 11/245* (2013.01); *B28B 13/06* (2013.01); *G01N 3/08* (2013.01); *G01N 2203/0266* (2013.01); *G01N 2203/0298* (2013.01); *Y10S 249/04* (2013.01)

(58) Field of Classification Search
CPC ... B28B 7/0094; Y10S 249/04; G01N 33/383; G01N 3/38; G01N 2203/0266; G01N 2203/0298

USPC ..... 249/DIG. 4, 164, 173, 117; 73/803, 818, 73/864.91; D15/136
See application file for complete search history.

(56) References Cited

U.S. PATENT DOCUMENTS

| | | | | | |
|---|---|---|---|---|---|
| 3,163,908 | A | * | 1/1965 | Lawmaster | ........... B28B 7/0094 249/115 |
| 3,490,577 | A | * | 1/1970 | Grikscheit | ......... B65D 75/5844 206/205 |

(Continued)

OTHER PUBLICATIONS

Patterson, H. L. "Evaluation of 'Protecto +' Styrene-Foam Concrete Cylinder Molds". Michaing Department of State Highways Research Project 67 NM-188. Research Report R-681. Sep. 9, 1968. Published [Online] Mar. 6, 2014. Accessed [Online] Jan. 2, 2017. <http://web.archive.org/web/20140306153010/http://www.michigan.gov/documents/mdot/R-681_428588_7.>.*

(Continued)

*Primary Examiner* — Jonathan Dunlap
(74) *Attorney, Agent, or Firm* — Doherty Wallace Pillsbury & Murphy P.C.

(57) ABSTRACT

A concrete test cylinder mold formed of expandable polystyrene and which is used to form geometrically uniform concrete test cylinders that accurately reflect the structural properties of the concrete mix used to form the test cylinders despite fluctuations in temperature to which the test cylinder may be exposed during formation within the mold. The mold is constructed and configured such that compression testing of the concrete test cylinder may be conducted while the cylinder is still in the mold. A specially designed heat shield may be used in unison with the concrete test mold to form, at least in part, a system by which heat further may be retained within the system during formation of the concrete test cylinder.

5 Claims, 19 Drawing Sheets

(56) References Cited

U.S. PATENT DOCUMENTS

| | | | | |
|---|---|---|---|---|
| 3,527,439 | A | * | 9/1970 | Lawmaster ............ B28B 7/0094 215/398 |
| 3,815,851 | A | * | 6/1974 | Girard ................... B28B 7/0094 249/121 |
| 4,534,225 | A | * | 8/1985 | Peacock ................... G01N 3/02 248/632 |
| D364,413 | S | * | 11/1995 | Ishida .......................... D15/136 |
| 7,694,580 | B2 | * | 4/2010 | Workman ................ G01N 3/02 73/760 |
| 2003/0218265 | A1 | * | 11/2003 | Garcia-Gutierrez .... E04G 13/02 264/35 |
| 2006/0163445 | A1 | * | 7/2006 | Branchesi ............ B28B 7/0014 249/117 |
| 2013/0192382 | A1 | * | 8/2013 | Bois ..................... G01N 33/383 73/803 |

OTHER PUBLICATIONS

UCSolutions. "Cylinder Mould 100 × 200". Published [Online] Apr. 26, 2013. Accessed [Online] Jan. 2, 2017. <http://web.archive.org/web/20130426135004/http://www.ucsolutions.com.au/product/8-cylinder-mould-100-x-200.php>.*

* cited by examiner

CONCRETE TEST CYLINDER MOLD, SYSTEM, AND METHOD OF USE

BACKGROUND TO THE INVENTION

1. Field of the Invention

The present disclosure relates to concrete testing methods and systems and, more particularly, provides a method and system for producing reproducible concrete test cylinders.

2. Background of the Invention.

In the construction of highways, buildings, and other structures utilizing concrete, it is necessary from time to time to test the strength of a sample of the poured concrete to ensure that it has sufficient structural strength required for a particular installation. The most common method of testing concrete has been to take a sample of fresh concrete from a mix at a construction site.

Specifically, fresh concrete is poured into a concrete test cylinder mold to form a cylindrical concrete test cylinder. Upon completion of the cylinder fabrication process, the poured concrete extends above the top of the concrete test cylinder mold. At this point, the concrete that extends above the top of the concrete test cylinder is manually struck off with a tamping rod. The concrete remaining in the test cylinder mold is then left to set. The following day the concrete test cylinder molds may be picked up and delivered to a laboratory where the concrete test cylinders are cured under laboratory conditions.

After curing, the concrete is removed from the cylinder and is tested for compressive strength. The compressive strength of the concrete test cylinders is a representation of the strength of the concrete placed in the structure.

The problem with the prior art concrete test cylinders that are produced in conventional concrete test cylinder molds is that the concrete test cylinders produced are subjected to fluctuating temperatures during their formation and cure and/or to temperature ranges that adversely affect the overall structural integrity of the concrete test cylinder. Additionally, the strength of conventionally formed concrete test cylinders is compromised due to the change in the specimen's water content, as some traditionally used molds may absorb water from the concrete test mix.

Another problem encountered by prior art molds used in the formation of concrete test cylinders is that such molds do not offer regularity and/or standardization in height, diameter, and smoothness. Accordingly, the prior art does not ensure that every sample is of the same height, diameter, and level. As a result, some concrete test cylinders are non-planar or have an oval diameter at the top of the mold. Accordingly, the accuracy of the test of the concrete test cylinder is reduced since the overall compressive strength of the concrete test cylinder can be erratic due to distribution caused by handling or transportation of the concrete test cylinder. Therefore, there exists a need in the art to improve the uniformity of a concrete test cylinder through the use of an efficient and cost effective product.

Nothing in the prior art provides the benefits attendant with the present invention. Therefore, it is an object of the present invention to provide an improvement which overcomes the inadequacies of the prior art devices and which is a significant contribution to the advancement of the art.

SUMMARY OF THE INVENTION

The above mentioned disadvantages and draw-backs of the prior art are alleviated or greatly overcome by a concrete test cylinder mold which is especially designed and adapted to produce reliable concrete test cylinders. The concrete test cylinder molds of the present disclosure are made from expandable polystyrene, and are formed of sufficient thickness on the top, side and bottom to hold the concrete cylinder test mix to a specific size while the mix cures. The expandable polystyrene is a natural insulator and can maintain the curing temperature far better than presently known molds. Additionally, as the expandable polystyrene has a minimal compressive strength, as compared to the compressive strength of the concrete, there is no need to remove the concrete test cylinder from the mold during compressive strength testing. The density of the expandable polystyrene is also selected to prevent the mold from absorbing water from the concrete test sample. The mold is configured to prevent tipping and to prevent injury to the concrete test cylinder during fabrication, handling, transport, and testing of the cylinder. In an exemplary embodiment, a release agent may be used to coat the mold to prevent the concrete from bonding to the mold during cure time; alternatively or additionally, a thin plastic sheet may be disposed on the inside surface of the mold to prevent such bonding.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

For a better understanding of these and other objects of the present invention, reference will be made to the detailed description of the present invention which is to be read in association with the accompanying drawings, wherein.

DETAILED DESCRIPTION OF THE INVENTION

Figure 1:
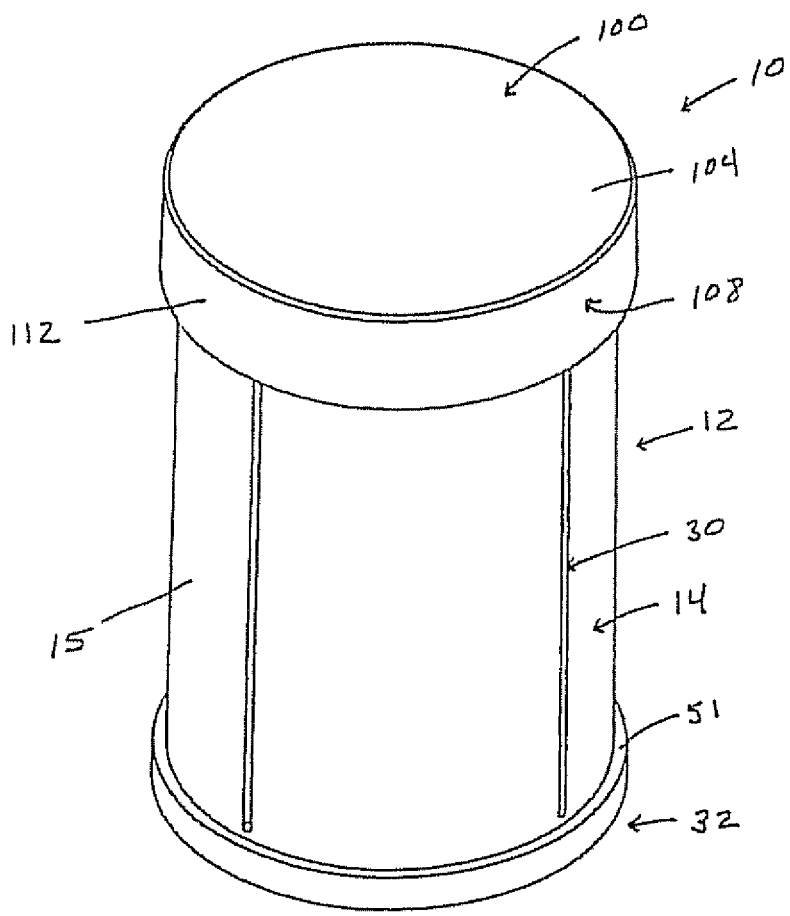
FIGS. 1 and 2 are schematics depicting an exemplary test cylinder mold.
Figure 2:
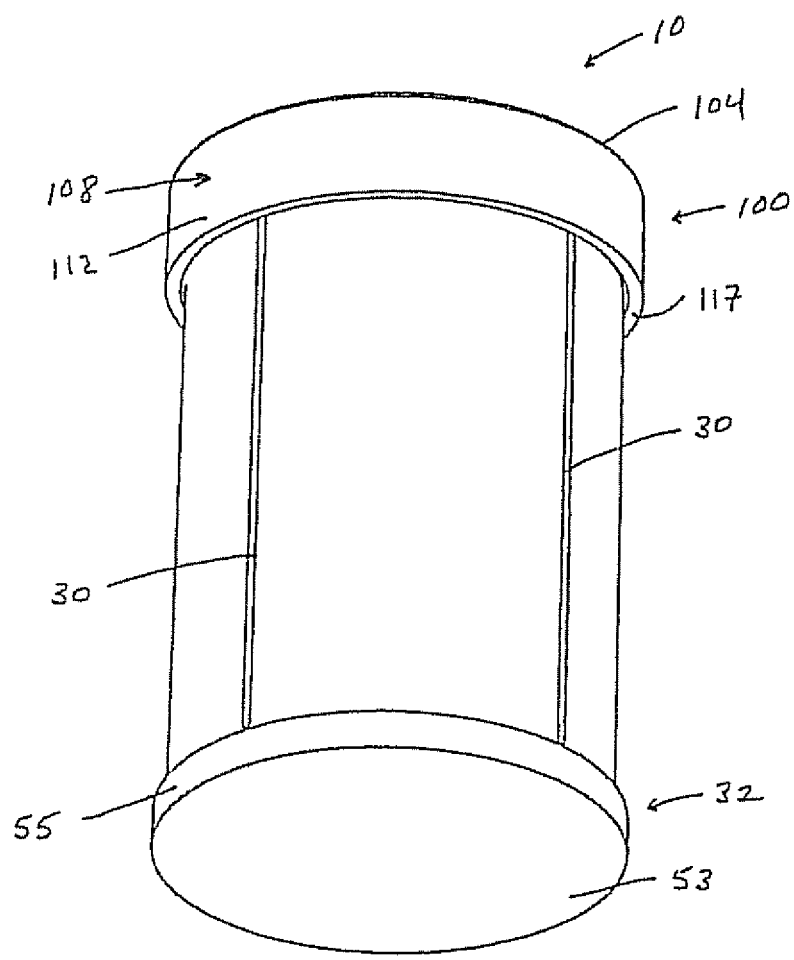

Disclosed herein is a concrete test cylinder mold that is specially configured to produce a concrete test cylinder that accurately and reliably reflects the properties of a concrete mix used at a work site for a particular construction. Further disclosed herein is a concrete test system comprising a concrete test cylinder mold and a concrete test cylinder, wherein the concrete test system may be subjected to compression testing useful in determining the compressive strength of the concrete test cylinder. Further disclosed herein is a concrete test assembly useful in forming the concrete test cylinder, wherein the assembly comprises the concrete test cylinder mold, the concrete test mix, and a heat shield. The heat shield is specially designed to further insulate the concrete test mix during cure of the concrete test mix.

The inventive concepts shall be more particularly described with reference to the drawings, wherein it is to be understood that the invention is not to be limited thereby, but shall include all modifications and variations thereto as would be evident to a person of ordinary skill in the art upon reading the present disclosure.

Referring to FIGS. 1-6, an exemplary concrete test cylinder mold 10 comprises a main body 12. Main body 12 has a generally frusto-conical shaped side wall 14 having an exterior side 15 oppositely situated to an interior side 17, and an anterior terminal end 21 oppositely situated to a posterior terminal end 25. Side wall 14 tapers inwardly as it extends from posterior terminal end 25 to anterior terminal end 21, and, therefore, posterior terminal end 25 has an outer diameter greater than an outer diameter of anterior terminal end 21. Main body 12 further comprises a generally cylindrical-shaped chamber 27 surrounded by interior side 17 and which extends the length of interior side 17.

Main body 12 further comprises a plurality of grooves 30. Each of the grooves of plurality 30 is formed through an outer edge 22 of anterior terminal end 25 and extends longitudinally on exterior side 15 of side wall 14 short of extending through posterior terminal end 25. In a preferred embodiment, the grooves of plurality 30 are radially and regularly spaced around exterior side 15 of main body 12, and are formed parallel with one another. Plurality of grooves 30 assists in the removal of the concrete test cylinder from mold 10, such as may be desired after the concrete test cylinder has been tested for compressive strength.

Concrete test cylinder mold 10 further comprises a base 32. Base 32 comprises a substantially circular-shaped body having a top side 51 oppositely situated to a bottom side 53 and joined thereto via a side wall 55 that is contiguously formed with and substantially perpendicular to top and bottom sides 51 and 53. Side wall 55 comprises an outer diameter greater than an outer diameter of side wall 14. Top side 51 is contiguously and coaxially formed with posterior terminal end 25 of side wall 14, such that side wall 14 is recessed relative to side wall 55.

Main body 12 and base 32 are formed of expanded polystyrene. In an exemplary embodiment, the expandable polystyrene has a density of about 1.5 pounds per cubic foot. Furthermore, in an exemplary embodiment, the expandable polystyrene used to form mold 10 comprises beads having a range in diameter of about 0.063 inch to about 0.188 inch, wherein about 0.063 inch to about 0.125 inch is more preferred, and about 0.063 inch to about 0.100 inch is especially preferred. The expandable polystyrene is preferably formed of a modified grade of expandable polystyrene, and, hence, has fire retardant properties.

Figure 7:
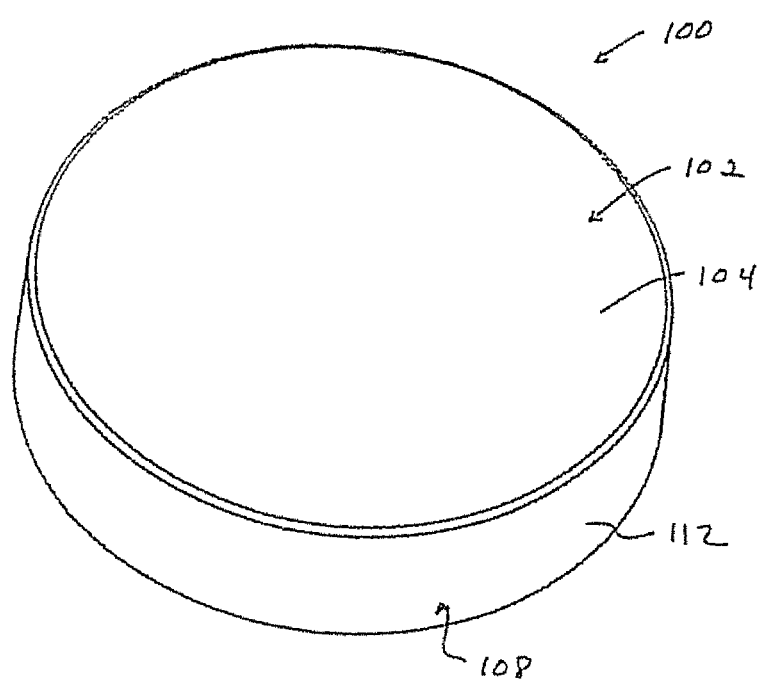
FIG. 7 is a schematic depicting an elevational view of a top side of an exemplary lid.
Figure 8:
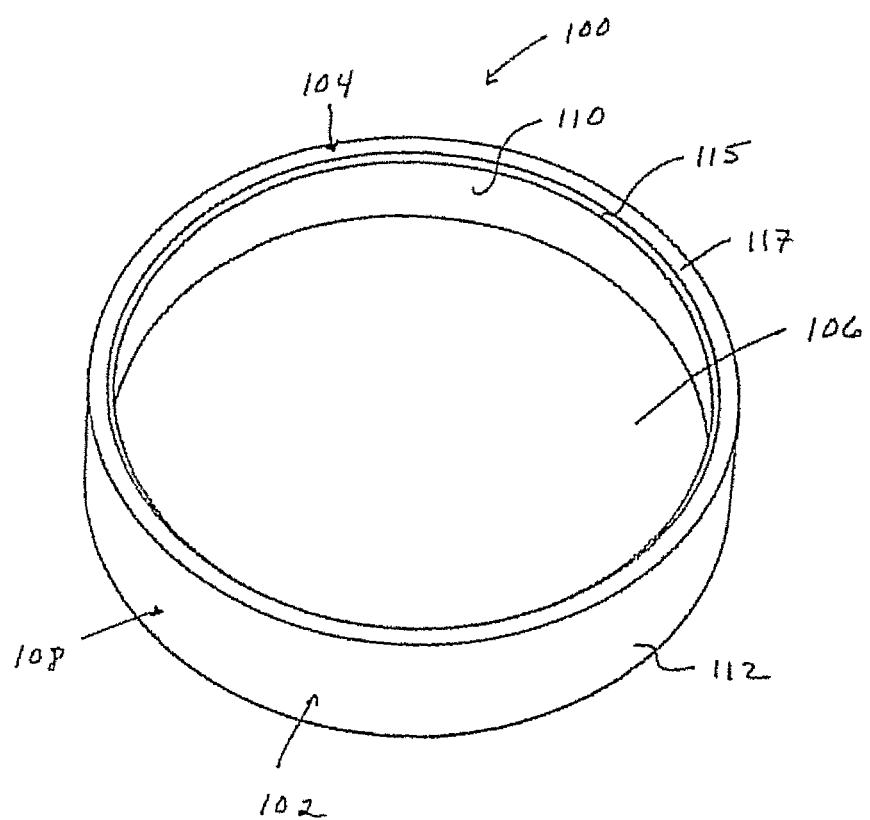
FIG. 8 is a schematic depicting an elevational view of a bottom side of the lid depicted in FIG. 4.
Figure 9:
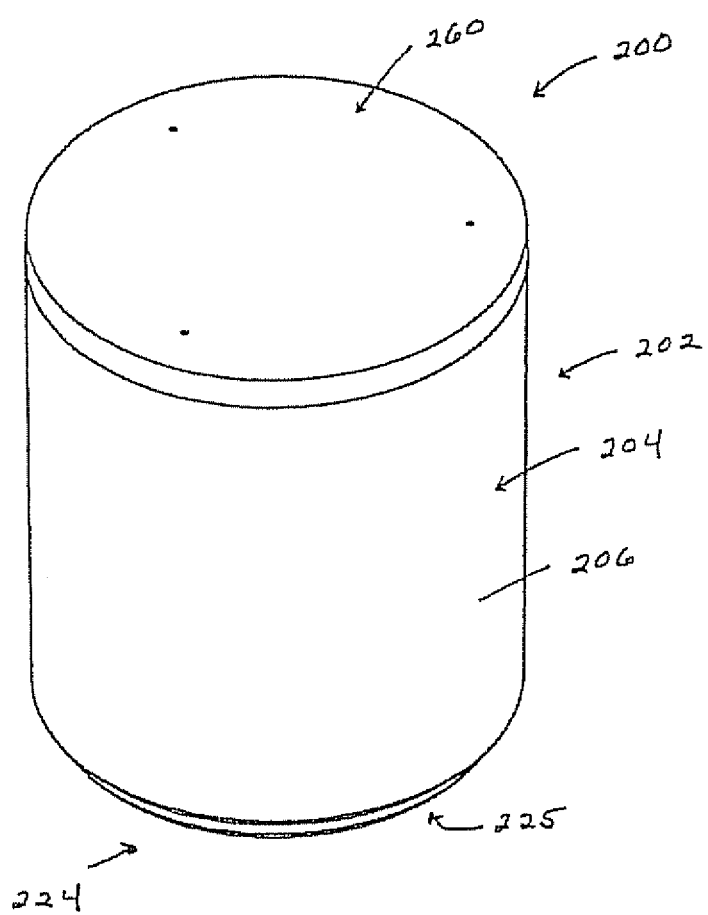
FIGS. 9 and 10 are schematics depicting an exemplary heat shield.
Figure 10:
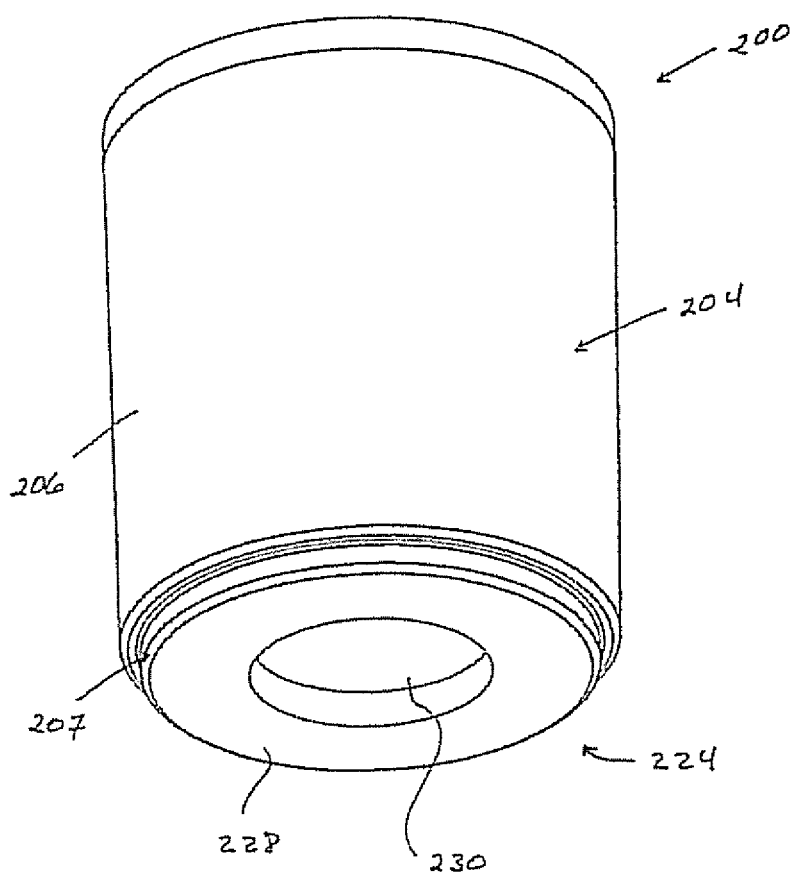
Figure 11:
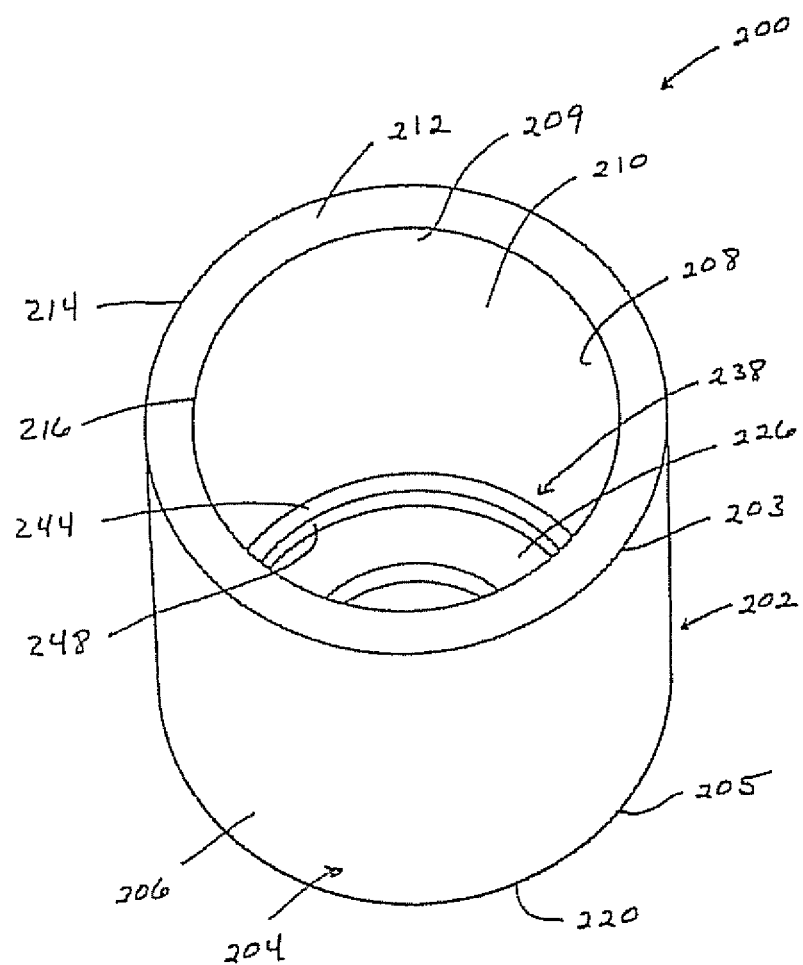
FIG. 11 is a schematic depicting an elevational top view of a portion of the exemplary heat shield depicted in FIGS. 9 and 10.
Figure 12:
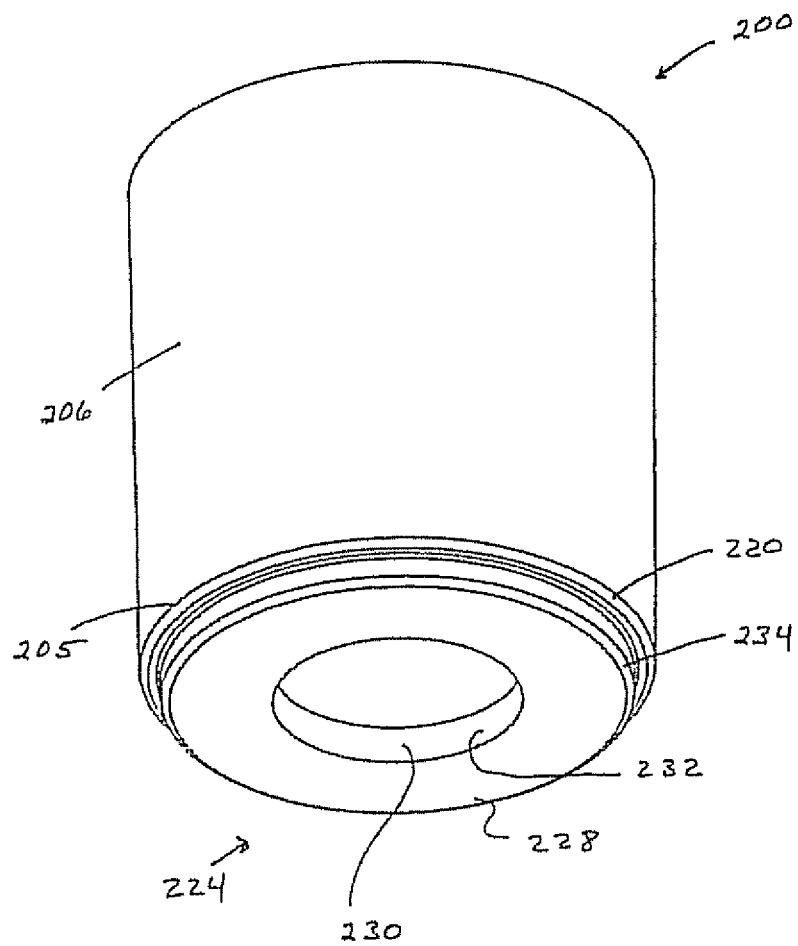
FIG. 12 is a schematic depicting an elevational bottom view of a portion of the heat shield depicted in FIGS. 9 and 10.
Figure 13:
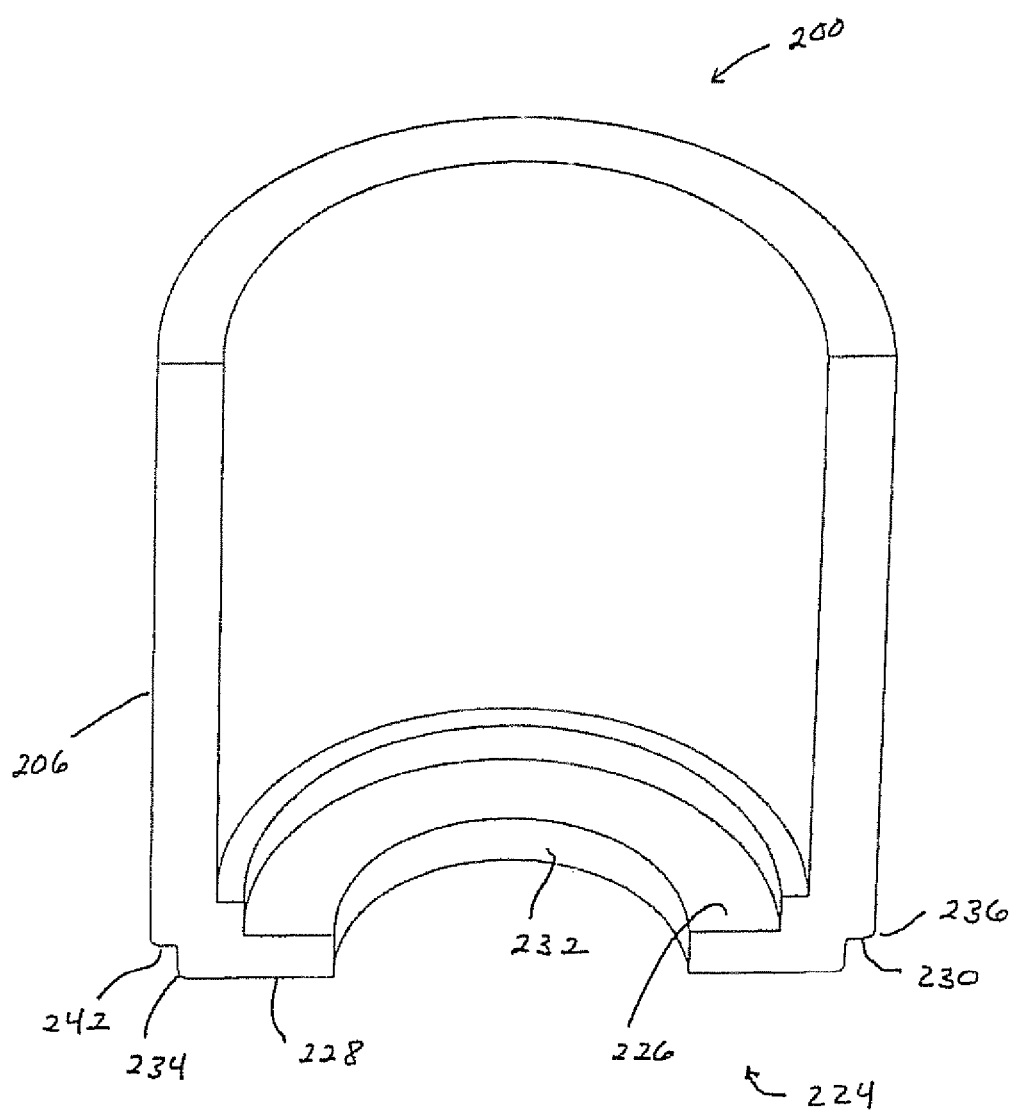
FIG. 13 is a schematic depicting a longitudinal section of the heat shield depicted in FIGS. 11 and 12.

Referring to FIGS. 7 and 8, concrete test cylinder mold 10 may further comprise a lid 100 which may be secured over anterior terminal end 21 of main body 12. Lid 100 comprises a generally circular shaped body 102 having a top face 104 oppositely situated to a bottom face 106. Lid 100 further comprises an annular shaped side wall 108. Side wall 108 comprises an interior side 110 contiguously formed with an outer perimeter of bottom face 106, and an exterior side 112 contiguously formed with an outer perimeter of top face 104. An annular-shaped bottom wall 114 is contiguously formed with and positioned transversely to side wall 108. Bottom wall 114 comprises a sloped portion 115 contiguously formed with a substantially planar portion 117, wherein sloped portion 115 is also contiguously formed with interior side 110 and slopes upwardly from interior side 110 towards substantially planar portion 117. Substantially planar portion 117 is contiguously formed with exterior side 112 and is parallel to top and bottom faces 104 and 106. A space 116 is formed between and extends from bottom face 106 and bottom wall 114.

Figure 3:
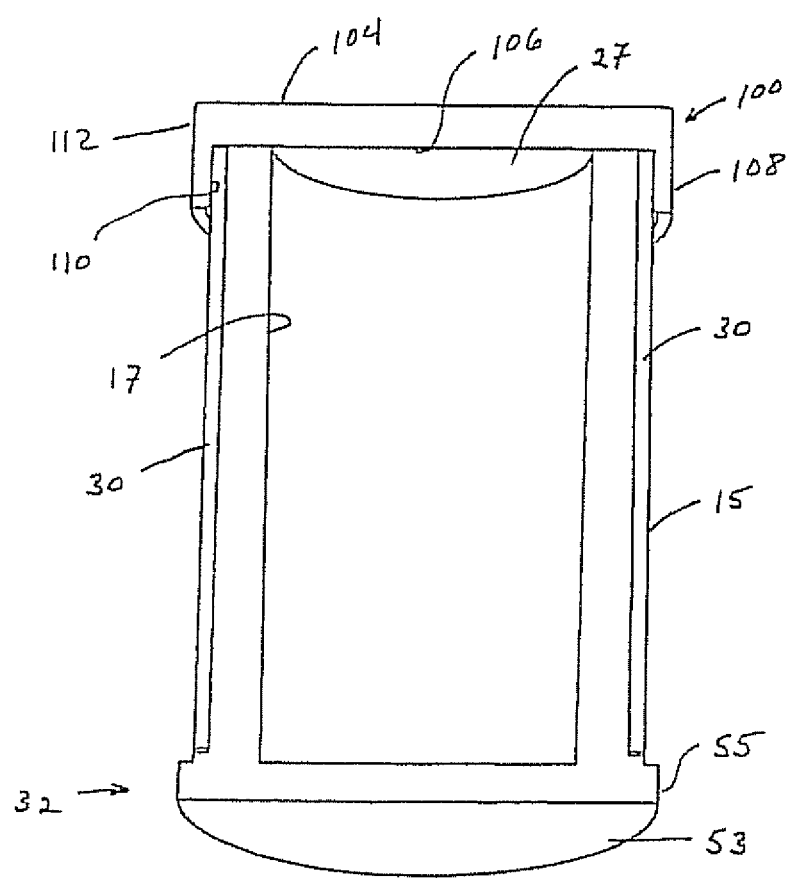
FIG. 3 is a schematic depicting a longitudinal section of the test cylinder mold depicted in FIGS. 1 and 2.
Figure 4:
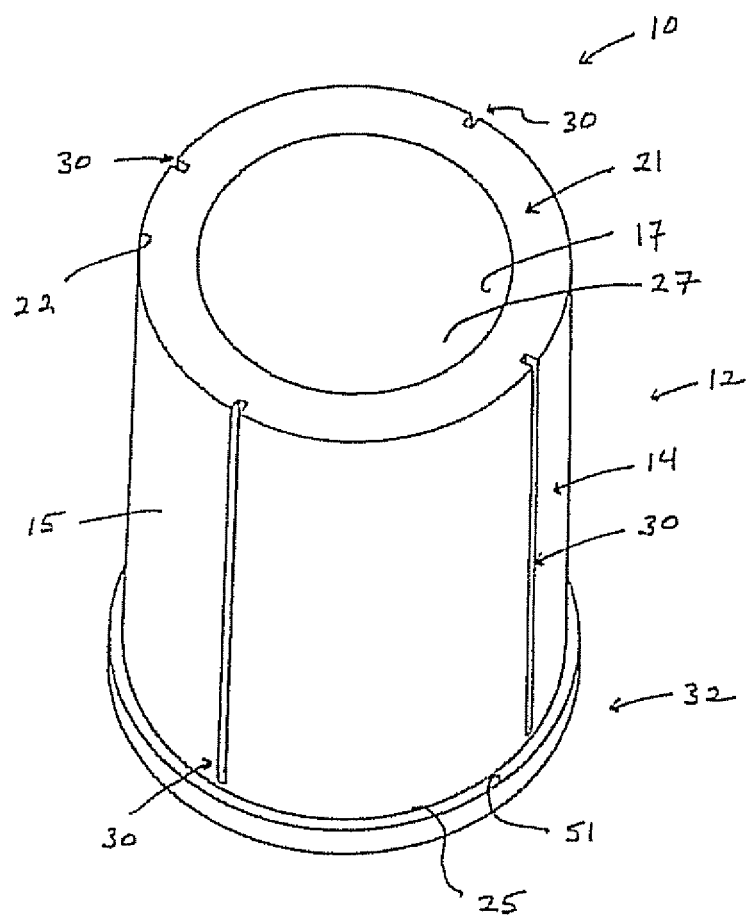
FIG. 4 is a schematic depicting an elevational view of a portion of the test cylinder mold depicted in FIGS. 1-3.
Figure 5:
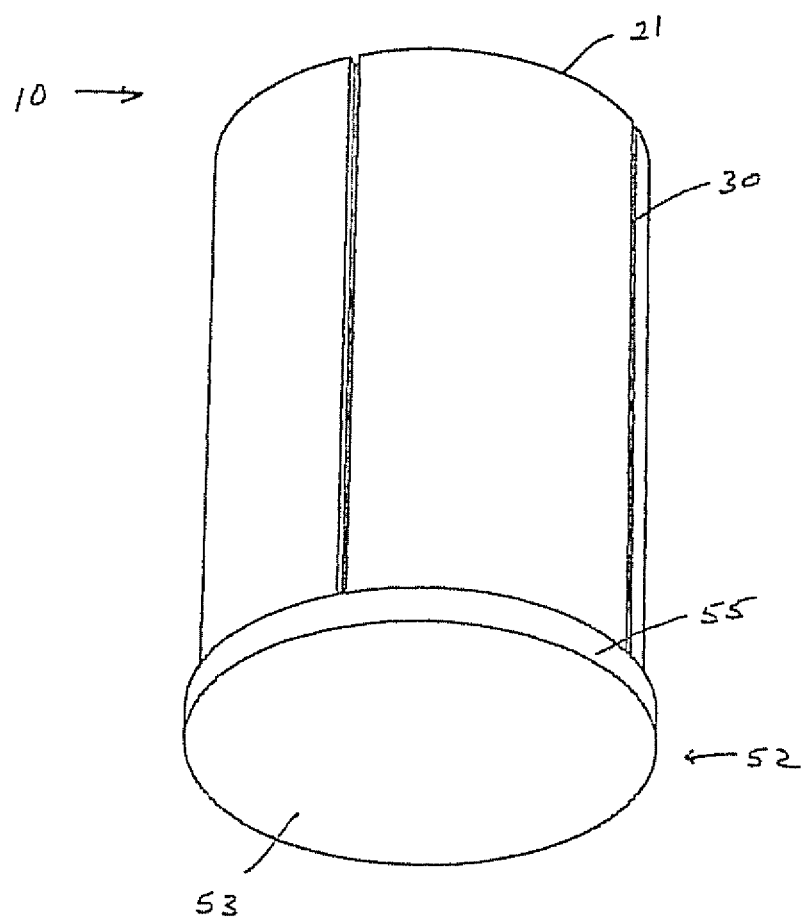
FIG. 5 is a schematic depicting an elevational view of a bottom side of the test cylinder mold depicted in FIGS. 1-3.
Figure 6:
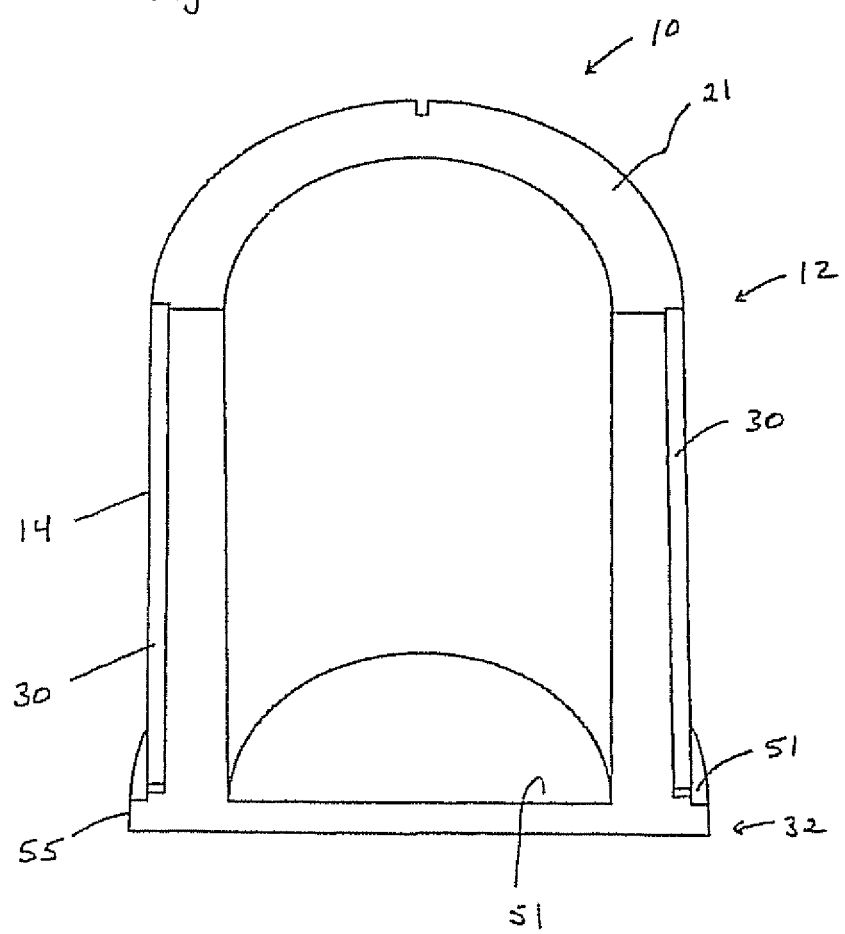
FIG. 6 is a schematic depicting a longitudinal section of the test cylinder mold depicted in FIGS. 1-3.

Referring to FIG. 3, lid 100 is configured and dimensioned such that when received by concrete test cylinder mold 10, side wall 108 overhangs exterior side 15 of side wall 14 of mold 10, interior side 110 of side wall 108 physically abuts exterior side 15 of side wall 14, and bottom face 106 physically abuts anterior terminal end 125. Bottom face 106 and top side 51 of base 32 are preferably in parallel alignment with one another to thereby ensure that the top and bottom sides of the concrete test cylinder formed within mold 10 are parallel with each other, thereby assisting in the creation of a uniformly shaped concrete test cylinder.

To form the concrete test cylinder, a concrete mix is poured into chamber 27 of mold 10. The concrete mix may be evenly distributed within chamber 27 via a rod member as is conventionally known in the art. Lid 100 may be positioned on main body 12 of mold 10 as described above, and the concrete mix may be allowed to cure to form the concrete test cylinder.

In an exemplary embodiment, prior to placement of the concrete mix into mold 10, at least one of main body 12, base 32, and lid 100, and more preferably at least main body 12 of mold 10, is coated with a release agent. The release agent serves to lubricate the expanded polystyrene. Additionally or alternatively, a thin plastic sheet may be placed on the inside surface of at least one of main body 12, base 32, and lid 100 of mold. Either or body of the release agent and the thin plastic sheet serves to prevent the concrete from sticking to mold 10 during the concrete's curing time within mold 10.

Figure 19:
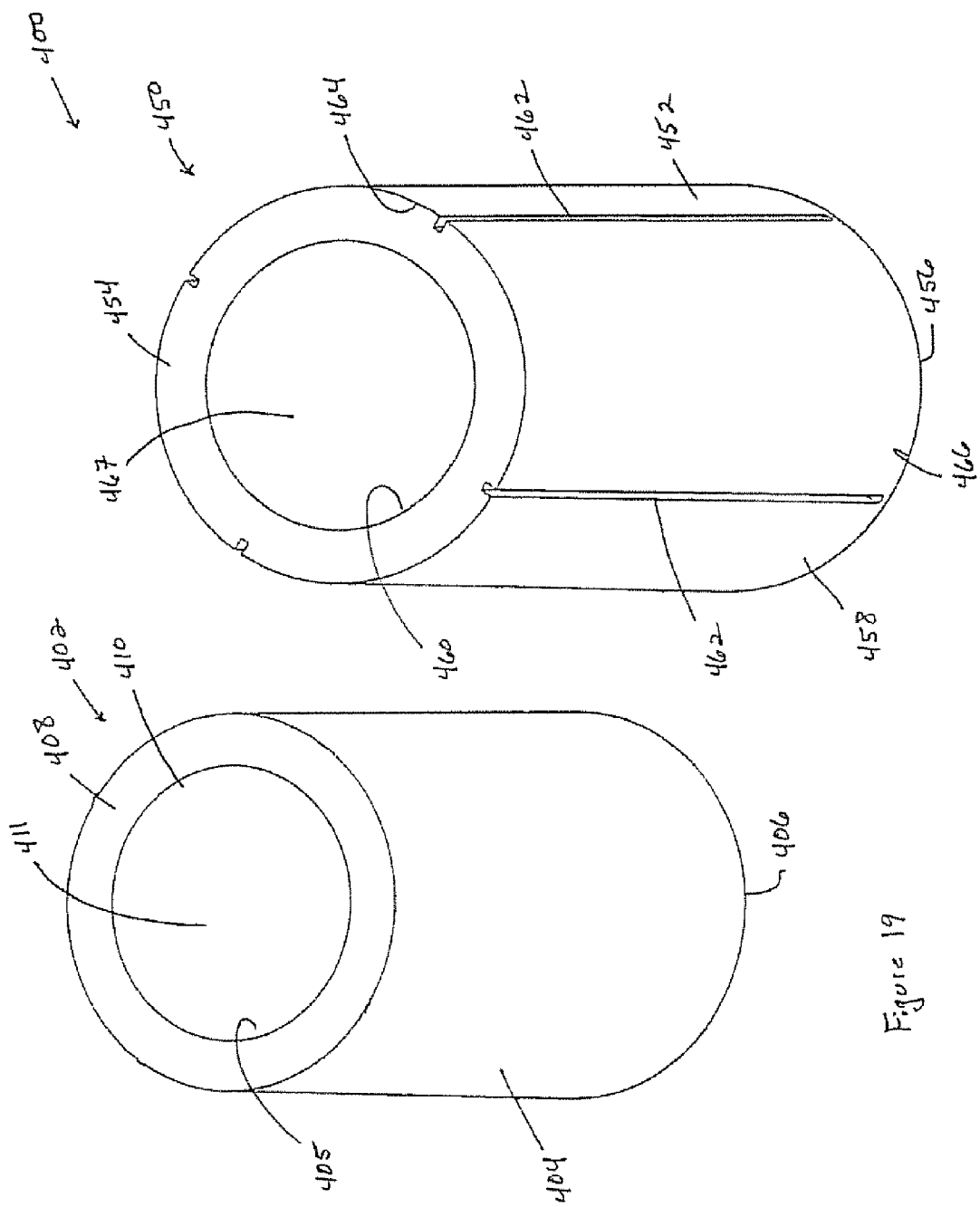
FIG. 19 is a schematic depicting an exemplary test cylinder mold assembly.

Referring to FIG. 19, an exemplary concrete test cylinder mold assembly 400 comprises a mold 450 having a substantially cylindrically shaped body 404 flanked on one end thereof by a bottom side 406 and on an oppositely situated end by an open-ended top side 408. Top side 408 has an opening 410 formed therein which leads into a chamber 411. Mold 450 is formed from expandable polystyrene.

Assembly 400 further comprises a sleeve 402. Sleeve 402 comprises a substantially cylindrical shaped body 452 having an open ended top side 454 oppositely situated to an open ended bottom side 456, and an exterior wall 458 oppositely situated to an interior wall 460.

Exterior wall 458 has a plurality of grooves 462 formed therethrough. Each of the grooves of plurality 462 is formed at anterior terminal edge 464 and longitudinally extends therefrom on exterior wall 458 towards a posterior terminal edge 466. In a preferred embodiment, the grooves of plurality 462 are radially and regularly spaced around exterior wall, and are formed parallel with one another. Plurality of grooves 462 assists in the removal of mold, such as may be desired after the concrete test cylinder has been tested for compressive strength.

A chamber 467 continuously extends from top side 454 to bottom side 456.

Sleeve 402 is formed from expandable polystyrene and serves to insulate mold 450 during the curing process of the concrete. In an exemplary embodiment, the expandable polystyrene has a density of about 1.5 pounds per cubic foot. Furthermore, in an exemplary embodiment, the expandable polystyrene used to form sleeve 402 comprises beads having a range in diameter of about 0.063 inch to about 0.188 inch, wherein about 0.063 inch to about 0.125 inch is more preferred, and about 0.063 inch to about 0.100 inch is especially preferred. The expandable polystyrene is preferably formed of a modified grade of expandable polystyrene, and, hence, has fire retardant properties.

To form the concrete test cylinder, mold 450 may be disposed within chamber 411 of sleeve 402 such that exterior wall 458 of mold 450 physically abuts an interior wall 405 of body 404 of sleeve 402, bottom side 456 physically abuts bottom side 406, and top side 454 is coplanar with top side 408. A concrete mix may be poured into chamber 467 of mold 450. The concrete mix may be evenly distributed within chamber 467 via a rod member as is conventionally known in the art. A lid (such as that described as suitable for use with mold 10) may be positioned over top side 454 of mold 450, and the concrete mix may be allowed to cure to form the concrete test cylinder.

The mold described herein protects the concrete mix inside the mold from temperature swings and from damage during handling. The density of the expandable polystyrene used to form the mold is high enough to prevent the expandable polystyrene from drawing water away from the concrete mix. Standard compressive tests can be performed on the mold and the concrete test cylinder formed therein using the same procedures as are done with traditionally used plastic or metal containers. The ability of the heat of hydration of the concrete while curing in the mold formed of expandable polystyrene allows the temperature of the concrete mix to cure at a more uniform temperature for a longer period of time as compared to the temperature of concrete cured in conventional molds, particularly when the molds are exposed to temperatures below 32 degrees Fahrenheit, as the expandable polystyrene maintains the heat of hydration within the mold during curing.

An outer protective heat shield formed of expandable polystyrene can provide an additional method to maintain the concrete cylinder at a temperature higher than current cylinder designs under cold weather conditions. Accordingly, further disclosed herein is a heat shield that is specially designed to be used in combination with the various mold embodiments disclosed herein to further enhance the conditions under which the concrete test cylinder is formed, and to, thereby, protect the integrity of the concrete test cylinder during its formation.

Referring to FIGS. 9-13, an exemplary heat shield 200 comprises a generally cylindrical shaped body 202 having a side wall 204. Side wall 204 has an anterior terminal end 203 oppositely situated to a posterior terminal end 205. Side wall 204 further has an exterior side 206 oppositely situated to an interior side 208, wherein interior side 208 surrounds a chamber 210. Body 202 further comprises an open-ended top side 212 contiguously formed with anterior terminal end 203 and having an opening 209 coaxial with chamber 210. Top side 212 has an outer edge 214 oppositely situated to an inner edge 216, wherein inner edge 216 is contiguously formed with interior side 208 and outer edge 214 is contiguously formed with exterior side 206. Posterior terminal end 205 turns substantially perpendicularly inwardly towards chamber 210 to form a bottom side 220 of bottom 202. Bottom side 220 turns substantially perpendicularly away from top side 212 to form a footing 224.

Footing 224 has a lower substantially ring-shaped member 225. Member 205 comprises a top side 226 oppositely situated to a bottom side 228, and a substantially annular-shaped side wall 207 contiguously formed with top and bottom sides 226 and 228 and positioned transversely thereto. Top side 226 is coplanar with bottom side 220 of body 202. Side wall 207 comprises an exterior side 234 oppositely situated to an interior side 232. Exterior side 234 is directed to exterior side 206 and is recessed relative thereto, thereby forming an outer flange 236 between exterior side 206 and exterior side 234. Member 205 further comprises an opening 230 formed through top and bottom sides 226 and 228 and immediately surrounded by interior side 232, wherein opening 230 is coaxial with chamber 210 and has a diameter less than the diameter of chamber 210.

Heat shield 200 further comprises an interior annular member 238 which is contiguously and continuously formed along a perimeter of interior side 208 of side wall 204, and which is contiguously and continuously formed with top side 226 of footing 224. Interior annular member 238 comprises an interior side wall 248 contiguously formed with top side 226 of footing 224 and which extends substantially perpendicularly therefrom towards top side 212 of heat shield 200. Interior annular member 238 further comprises a top side 244 which is perpendicularly formed with interior side wall 248 and that is contiguously formed with interior side 208 of side wall 204.

Figure 14:
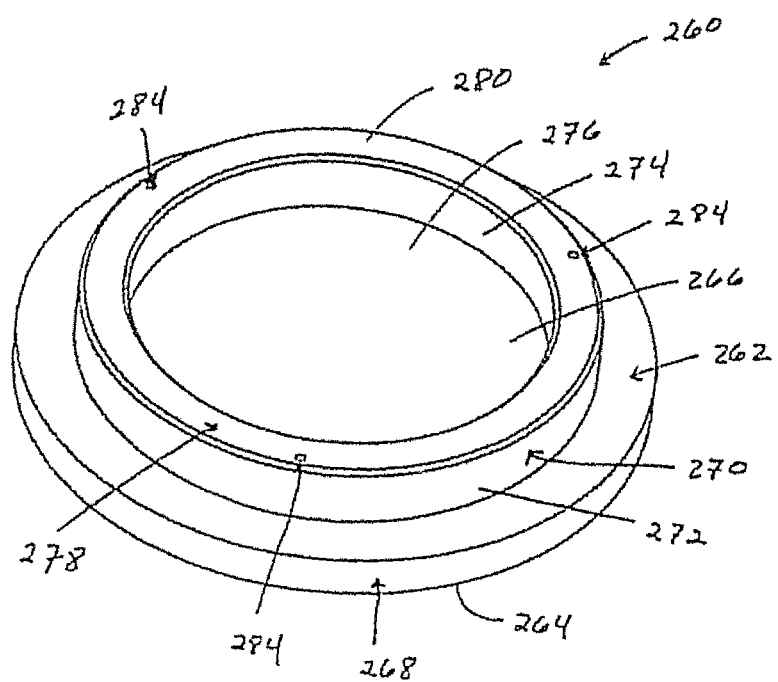
FIGS. 14-16 are schematics depicting an exemplary cap for the heat shield depicted in FIGS. 11-13.
Figure 15:
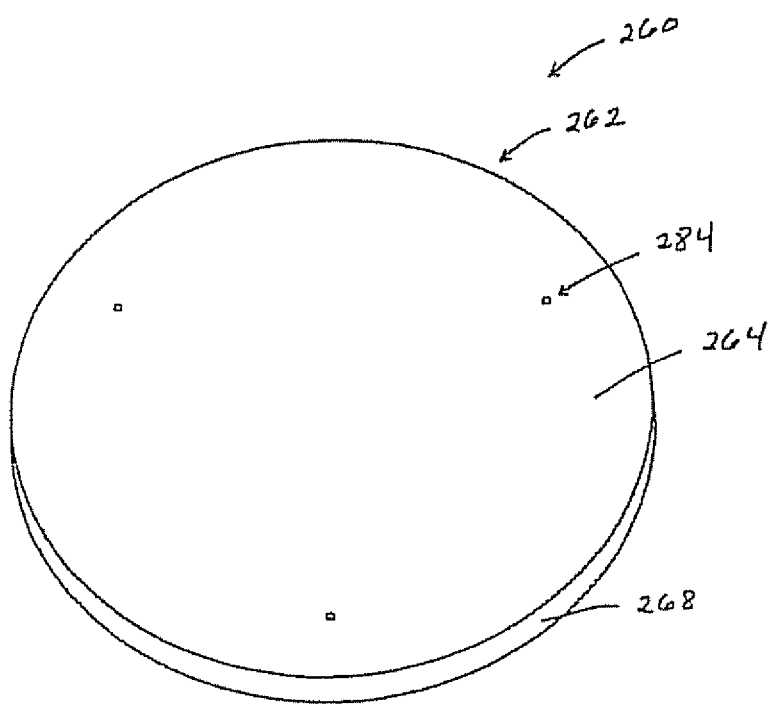
Figure 16:
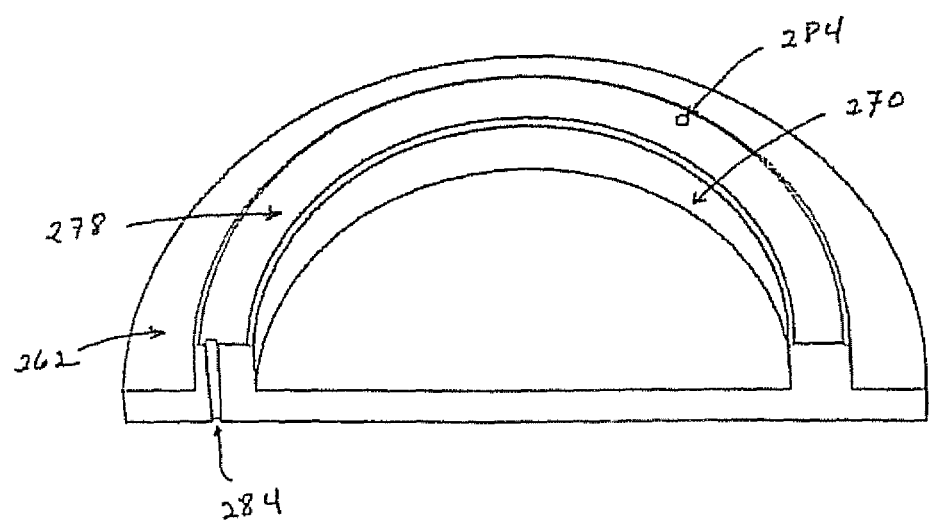

Referring to FIGS. 14-16, heat shield 200 may further comprise a cap 260 which may be secured to body 202 of heat shield 200. Cap 260 comprises a generally circular shaped upper member 262 having a top side 264 oppositely situated to a bottom side 266 and joined thereto by a side wall 268. Centrally disposed and contiguously formed on bottom side 266 is a lower member 270 having a generally annular shaped configuration. Lower member 270 has an annular shaped exterior side wall 272 oppositely situated to an annular shaped interior side wall 274.

Cap 260 further comprises a generally annular shaped lip 278 contiguously formed with lower member 270 and positioned opposite to upper member 262. Lip 278 comprises a face 280 that is directed opposite to upper member 262 and transversely to side walls 272 and 274 of lower member 270, and which is recessed relative to exterior and interior side walls 272 and 274. Cap 260 further comprises a space 276 immediately surrounded by interior side wall 274 and that extends from bottom side 266 of upper member 262 to face 280 of lip 278.

Upper member 262 comprises an outer diameter greater than an outer diameter of lower member 270. Accordingly, exterior side wall 272 of lower member 270 is recessed relative to side wall 268 of upper member 262.

Cap 260 further comprises a plurality of channels 284. Each channel of plurality 284 extends from top side 264 of upper member 262 to face 280 of lip 278, and through lower member 270. Plurality of channels 284 allows air to enter an air space between exterior side 15 of mold 10 and interior side 208 of heat shield 200. This embodiment is particularly useful where air activated heat pads are used as an additional source for heat as will be described below in further detail.

In an exemplary embodiment, heat shield 200, which includes body 202, footing 224, interior annular member 238, and cap 260, comprises expandable polystyrene, wherein an exemplary expandable polystyrene has a density of about 1.5 pounds per cubic foot, and has the same properties as was described above with reference to mold 10.

Figure 17:
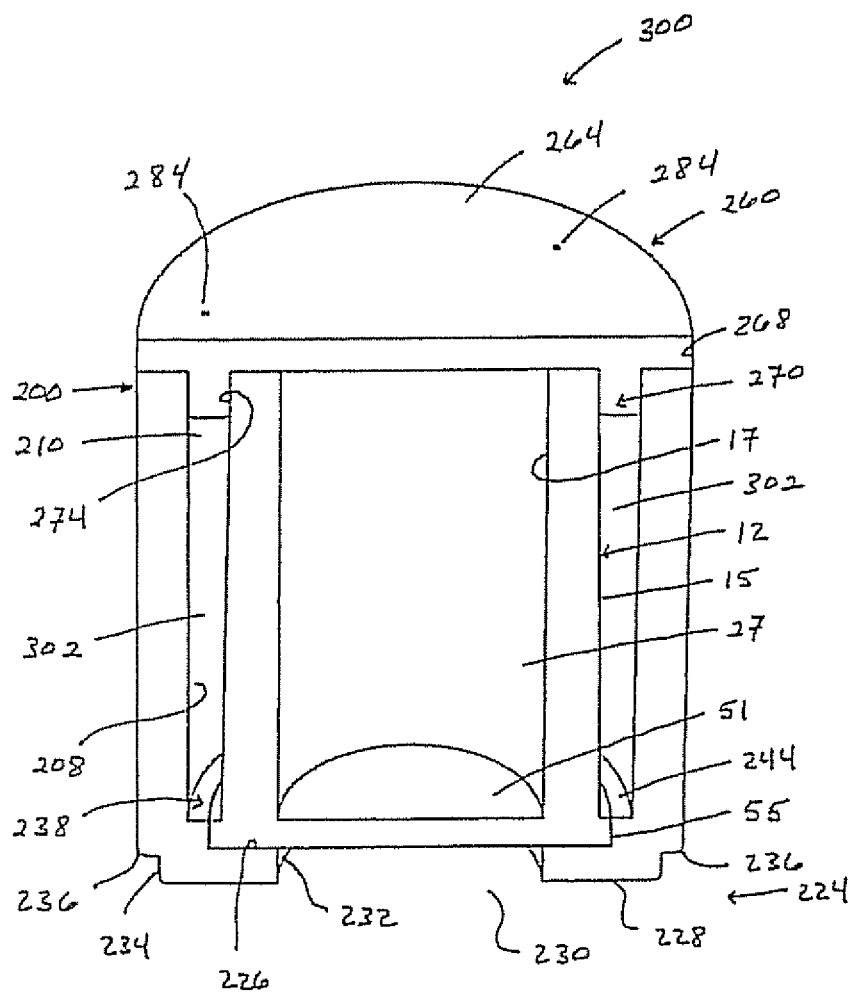
FIG. 17 is a schematic depicting a longitudinal section of an exemplary system.
Figure 18:
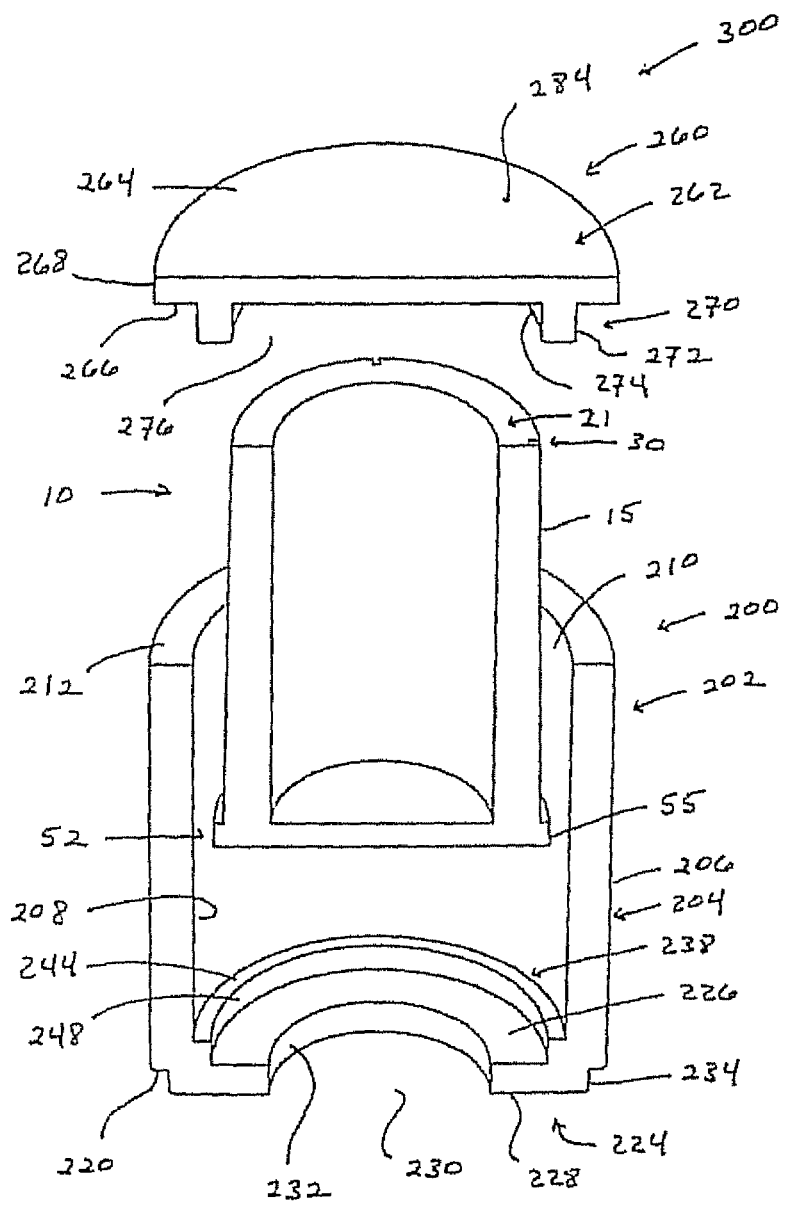
FIG. 18 is a schematic depicting an exploded view of the system depicted in FIG. 17.

Referring to FIGS. 17 and 18, an exemplary system 300 comprises concrete test cylinder mold 10 and heat shield 200. Heat shield 200 receives mold 10 through chamber 210. When properly disposed within body 202 of heat shield 200, bottom side 53 of base 52 of mold 10 is disposed on top side 226 of footing 224 such that side wall 55 of base 52 physically abuts interior side wall 248 of interior annular member 238. An air space 302 is created between interior side wall 208 of heat shield 200 and exterior side 15 of mold 10. Cap 260 is positioned atop body 202 such that bottom side 266 of cap 260 physically abuts top side 212 of body 202 and anterior terminal end 21 of mold 10, and such that lower member 270 of cap 260 extends within air space 302 such that exterior side wall 272 physically abuts interior side 208 of body 202 and interior side wall 274 physically abuts exterior side 15 of mold 10. Plurality of channels 284 are in fluid communication with air space 302.

Heat shield 200 may also be used in combination with assembly 400 in substantially the same was as heat shield 200 was used with test cylinder mold 10.

In another exemplary embodiment, system 300 may further comprise one or more heating pads that may be disposed within air space 302 to input thermal energy into system 300 to maintain proper curing temperature within the system as the concrete poured within mold 10 cures. The heating pads may be activated by, e.g., at least one of electrical, mechanical means, and chemical means. Exemplary chemically-activated heating pads may comprise at least one of, e.g., iron powder, activated carbon, remiculite, a salt, and the like. When the one or more chemically-activated heating pads are exposed to air, which enters system 300 via holes 284, a chemical reaction occurs which produces heat. Alternatively or additionally, the one or more chemically-activated heating pads may have one or more pouches that start the heating process when the materials within the one or more pouches are placed into air space 302.

The concrete test cylinder mold of the present disclosure has several advantages over currently known molds. For example, the expandable polystyrene used to form the mold comprises a density which has been optimized to prevent the mold from absorbing water in the concrete test mix.

Additionally, use of expandable polystyrene in the formation of the mold provides an insulating effect, thereby insulating the concrete test mix from dramatic fluctuations in temperature, thereby maintaining the integrity of the concrete test mix during its formation into the concrete test cylinder. Additionally, ASTM standards require that the concrete test cylinder formed within a mold be allowed to cure for up to 48 hours at an exterior temperature range of between about 60 degrees Fahrenheit to about 80 degrees Fahrenheit. Therefore, as expandable polystyrene has strong insulating properties, the molds disclosed herein may be used to cure the concrete test cylinders at any time of the calendar year as they readily can meet the ASTM's temperature range.

In addition to the benefits derived from the use of expandable polystyrene, the mold of the present disclosure has certain advantages based upon its physical design. For example, the mold of the present disclosure comprises a base that is configured to rest firmly on the ground when in use and to resist tipping over when the concrete test mix is poured into the mold. Additionally, the mold is constructed to survive rough handling during consolidation of the poured concrete mix into the mold, e.g., when the concrete mix is subjected to blows from a rod used to mix and consolidate the concrete test mix in the mold, and during the removal, transport, and delivery of the mold and concrete mix to the testing facility, and to protect the concrete test cylinder from damage. Nonetheless, in an exemplary embodiment, the mold may include a support member disposed within the chamber of the mold and positioned on the top side of the base. The support member is designed to protect the mold from forces sustained by the mold when the tamping rod is used with excessive force. In an exemplary embodiment, the support member comprises a generally disc-shaped configuration and is formed of a plastic material.

The mold is further designed to facilitate the placement and visibility of a label thereon, wherein the label bears information relevant to the testing and/or identification of the concrete test cylinder. Additionally, the lid and the base of the mold are configured to assure that the surfaces are parallel to one another once the cover is placed on the cylinder thereby ensuring that the concrete test cylinder has a uniform configuration. Additionally, the lid is designed to fit firmly on the mold to prevent accidental dislodgement.

As the compressive strength of the mold formed out of expandable polystyrene is minimal and insignificant compared to the compressive strength of the concrete test cylinder (i.e., the compressive strength of the concrete test cylinder is at a minimum of about 281 times stronger than the compressive strength of the mold), when the concrete test cylinder is ready for testing, the complete system, e.g., the mold and the concrete test cylinder, may be placed in a conventionally known and used compression testing machine and the compressive strength may be tested by conventional means. For example, an exemplary method for testing the compressive strength of the concrete test cylinder includes providing a compression testing machine having rings located at the top and bottom of the machine, wherein, during compression, the rings applies a uniform load to the concrete test cylinder. The compression testing machine may be hydraulic and may gradually add weight to the top of the concrete test cylinder and the gauge measures the weight that the concrete test, cylinder is bearing. The gauge then measures the weight at which the concrete test cylinder fails, which is the weight at which the concrete test cylinder cracks and breaks. Different compositions of concrete made for different applications have different weight requirements, which may range from about 1,000 pounds per square foot to about 10,000 pounds per square foot.

The foregoing description of the preferred embodiment of the invention is to be considered as illustrative and not as limiting. Various other changes and modifications will occur to those skilled in the art for performing substantially the same function, in substantially the same way, to achieve substantially the same result without departing from the true scope of the invention as defined in the appended claims.

What is claimed is:

1. A system for forming a concrete test cylinder comprising:
   a concrete test cylinder assembly comprising:

a mold formed, at least in part, of expanded polystyrene, and further comprising a generally cylindrical shaped body having an exterior wall oppositely situated to an interior wall, and an open-ended top side oppositely situated to a bottom side, wherein the top side and the bottom side of the mold are positioned transverse to the exterior and, interior walls of the mold, and further wherein a chamber is coterminously formed with the top and bottom sides of the mold and is immediately surrounded by the interior wall of the mold; and a sleeve formed, at least in part, of expanded polystyrene, and further comprising a generally cylindrical shaped body defined by an exterior wall oppositely situated to an interior wall, and by an open-ended top side and an oppositely situated open-ended bottom side, wherein the top and bottom sides of the sleeve are transverse to the exterior and interior walls of the sleeve, and, further wherein a uniformly formed cylindrical-shaped chamber is surrounded by the interior wall and is coterminous with the top and bottom sides of the sleeve;

wherein the mold is disposed in the chamber of the sleeve such that the exterior wall of the mold physically abuts the interior wall of the sleeve, and such that the bottom side of the mold is coterminous with the bottom side of the sleeve, and the top side of the mold is coterminous with the top side of the sleeve, wherein the chamber of the mold holds a concrete mix, and wherein the sleeve insulates the concrete mix during cure of the concrete mix; and a heat shield, wherein the heat shield comprises an expandable polystyrene material, and wherein the assembly is disposed within the heat shield.

2. The system of claim 1, wherein the heat shield comprises: a generally cylindrical-shaped body comprising an exterior side oppositely situated to an interior side, an open-ended top side oppositely situated to an open-ended bottom side, and a chamber surrounded by the interior, top, and bottom sides of the generally cylindrical-shaped body of the heat shield;

a generally annular-shaped footing contiguously formed with and transversely positioned to the bottom side of the body of the heat shield, wherein the footing comprises a top side oppositely situated to a bottom side, and an opening formed through the top and bottom sides of the footing thereby forming an interior side wall oppositely situated to an exterior side wall, wherein the opening is coaxial with the chamber of the heat shield, and further wherein the exterior wall of the footing is recessed relative to the exterior side of the body of the heat shield; and an interior annular member formed along a perimeter of the interior side of the body of the heat shield, wherein the interior annular member has a top side oppositely situated to a bottom side, and an opening formed through the top and bottom sides thereof and joined thereto by an interior side wall, wherein the opening of the interior annular member is coaxial with the chamber of the heat shield and with the opening of the footing, and further wherein the bottom side of the interior annular member is contiguously formed with the top side of the footing.

3. The system of claim 2, wherein the expandable polystyrene material of the heat shield comprises a density of about 1.0 pound to about 2.0 pounds per cubic foot.

4. The system of claim 3, wherein the heat shield further comprises a cap, wherein the cap comprises:

a generally circular shaped upper member having a top side oppositely situated to a bottom side, and joined thereto by a side wall;

a lower member having an annular shaped exterior side wall oppositely situated to an annular shaped interior side wall, wherein each of the annular shaped exterior and interior side walls of the lower member are contiguously and perpendicularly formed with the bottom side of the upper member of the cap, and further wherein the exterior side wall of the lower member has a diameter less than an outer diameter of the side wall of the upper member.

5. A method of testing compressive strength of a concrete test cylinder, wherein the method comprises:

providing the concrete test cylinder assembly of claim 1;

placing a concrete test mix within the chamber of the mold;

providing a heat shield, wherein the heat shield comprises a generally cylindrical shaped body having a chamber formed therein, wherein the generally cylindrical shaped body of the heat shield comprises an expandable polystyrene material;

placing the concrete test cylinder assembly and the concrete test mix, which has been placed within the chamber of the mold, within the chamber of the heat shield;

curing the concrete test mix to form a concrete test cylinder;

removing the concrete test cylinder assembly from the heat shield after the concrete test cylinder has formed and prior to placing the concrete test cylinder and the mold within a compression testing machine;

placing the concrete test cylinder, while it is still within the chamber of the mold, within the compression testing machine; and performing a compressive strength test.

* * * * *